United States Patent
Hilaire (10) Patent No.: US 7,335,182 B1
(45) Date of Patent: Feb. 26, 2008

(54) VALVED CONNECTOR WITH CLOSURE OPERATED BY AXIAL MOVEMENT OF THE VALVE

(75) Inventor: Pierre Hilaire, Paris (FR)

(73) Assignee: Arthesys, Gennevilliers (FR)

( * ) Notice: Subject to any disclaimer, the term of this patent is extended or adjusted under 35 U.S.C. 154(b) by 0 days.

(21) Appl. No.: 09/405,946

(22) Filed: Sep. 27, 1999

(30) Foreign Application Priority Data

Nov. 18, 1998 (EP) ................................. 98402855

(51) Int. Cl.
*A61M 1/00* (2006.01)
(52) U.S. Cl. ........................................................ 604/27
(58) Field of Classification Search ................. 604/167,
604/905, 27, 30, 33, 35, 36, 99.02, 167.02,
604/167.03, 167.04, 200, 201, 202, 204,
604/205, 206, 246, 247, 249, 250; 251/149.1,
251/149.5
See application file for complete search history.

(56) References Cited

U.S. PATENT DOCUMENTS

| | | | | |
|---|---|---|---|---|
| 4,512,766 A | * | 4/1985 | Vailancourt | 604/167.03 |
| 4,610,469 A | * | 9/1986 | Wolff-Mooij | 285/260 |
| 4,917,668 A | * | 4/1990 | Haindl | 604/167 |
| 4,935,010 A | * | 6/1990 | Cox et al. | 604/122 |
| 5,102,395 A | * | 4/1992 | Cheer et al. | 604/167 |
| 5,269,771 A | * | 12/1993 | Thomas et al. | 604/539 |
| 5,425,465 A | * | 6/1995 | Healy | 215/355 |
| 5,458,640 A | * | 10/1995 | Gerrone | 604/264 |
| 5,470,319 A | * | 11/1995 | Mayer | 604/167 |
| 5,492,147 A | * | 2/1996 | Challender et al. | 251/149.5 |
| 5,520,666 A | * | 5/1996 | Choudhury et al. | 604/537 |
| 5,613,663 A | * | 3/1997 | Schmidt et al. | 251/149.2 |
| 5,613,954 A | * | 3/1997 | Nelson et al. | 604/167 |
| 6,024,729 A | * | 2/2000 | Dehdashtian et al. | 604/256 |
| 6,050,978 A | * | 4/2000 | Orr et al. | 604/249 |

\* cited by examiner

*Primary Examiner*—Manuel Mendez
(74) *Attorney, Agent, or Firm*—James J. Leary; GSS Law Group (57) ABSTRACT

A valved connector apparatus is described having an integral opening and closing system operated by axial movement of the valve. The body of the valved connector apparatus is in a Y-shaped configuration with a main channel and a lateral channel branching off of the main channel. A normally closed, passive hemostasis valve is housed in a valve body that is slidably connected to the proximal end of the main channel. The hemostasis valve is opened by sliding the valve body distally with respect to the Y-shaped connector body so that a cylindrical extension extending from the proximal end of the Y-shaped connector body penetrates a central opening in the hemostasis valve, creating an open passage for insertion of guidewires, catheters or other instruments. The valved connector apparatus allows safe introduction of extremely flexible or fragile guidewires, catheters or other instruments.

21 Claims, 4 Drawing Sheets

VALVED CONNECTOR WITH CLOSURE OPERATED BY AXIAL MOVEMENT OF THE VALVE

FIELD OF THE INVENTION

The present invention relates to a valved connector with an integral opening and closing system operated by axial movement of the valve. The valved connector has many applications in the area of cardiovascular catheters and surgical instruments, particularly as a hemostasis valve on a cardiovascular catheter or introducer sheath. The valved connector can equally be used in connection with catheters and surgical instruments used in other body canals, such as the esophagus or urethra.

BACKGROUND OF THE INVENTION

It is frequently necessary in the course of catheterization procedures and many surgical procedures to insert one catheter or instrument through a passage or lumen in another catheter or instrument. To avoid bleeding or loss of other fluids through the annular space between the two catheters or instruments it is typical to employ a hemostasis valve or other sealing device at the proximal end of the outer catheter or instrument. The inner catheter or instrument is inserted through the hemostasis valve, which creates a fluid tight seal around the inner catheter or instrument. The hemostasis valve may be integrated into the outer catheter or instrument as is typical in the case of introducer sheaths, or it may be provided in a separate connector attachable to the outer catheter or instrument, as is typical for guiding catheters and many other cardiovascular catheters. A common configuration for such valved connectors is a Y-shaped configuration with a main channel that includes a hemostasis valve or other sealing device at its proximal end and a lateral channel that permits injection or aspiration of therapeutic or diagnostic fluids or measurement of pressure.

A problem arises when inserting a fragile or highly flexible catheter or instrument through such a hemostasis valve or sealing device. The fragile catheter or instrument may be deformed or damaged as it passes through the hemostasis valve or sealing device. In addition, many known valved connectors and fittings contain other obstacles to passage of a catheter or instrument, such as internal steps or cavities, abrupt tapers and side passages that may impede, divert or damage the catheter or instrument during insertion. This problem is of particular concern when using extremely flexible or fragile micro-guidewires and micro-catheters or when using assemblies mounted and maintained by friction or crimping, like for example a stent mounted on a balloon of a dilatation catheter.

Figure 1:
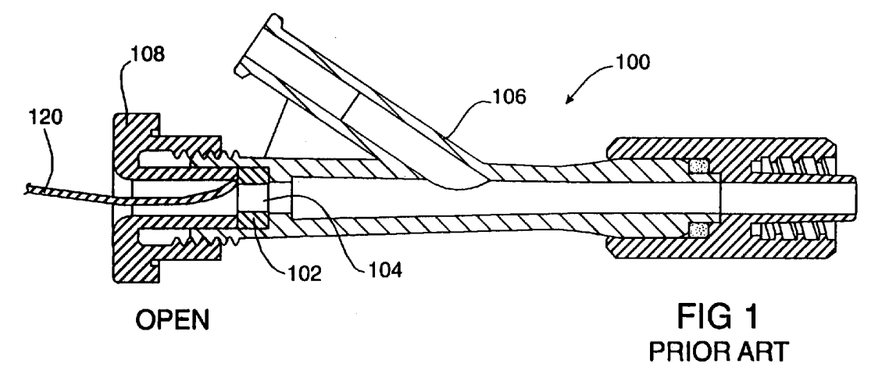
FIG. 1 shows a prior art valved connector of type 1 having a normally open valve, with the valve shown in the open position for introduction of a secondary device.
Figure 2:
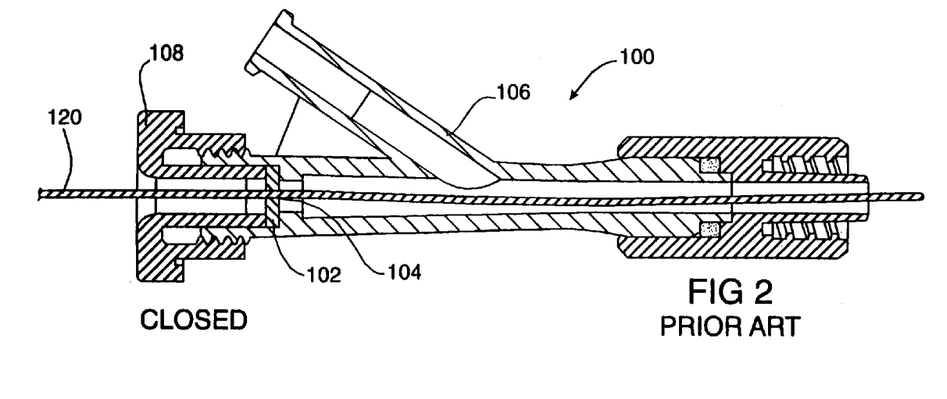
FIG. 2 shows the type 1 prior art valved connector of FIG. 1, with the valve shown in the closed position.

Hemostasis valves or sealing devices in existing valved connectors can be classified into two types:

The more common type, referred to herein as type 1, includes an active valve that is normally open and is closable by compressing a cylindrical or toroidal seal by means of a threaded cap. Adjusting the closure according to the diameter of the catheter introduced is accomplished by tightening or loosening the threaded cap as shown in FIGS. 1 and 2. Complete closure is possible even in the absence of an instrument introduced in the system.

The advantage of this system is that, when open, the valve provides an open passage for insertion of catheters and instruments. The disadvantage of this system is connected with the principle of the compression sealing mechanism. To permit the movement of the catheters introduced, one must loosen the threaded cap thereby provoking leaking of blood. Equally one must not forget to tighten the threaded cap to reclose the seal. These necessary manipulations are a significant inconvenience to the physician during a catheter procedure. Movement of the inserted catheter without loosening the valve can easily damage a delicate catheter or instrument. In addition, overtightening of the threaded cap can cause damage to the catheter or instrument introduced through the valve.

Figure 3:
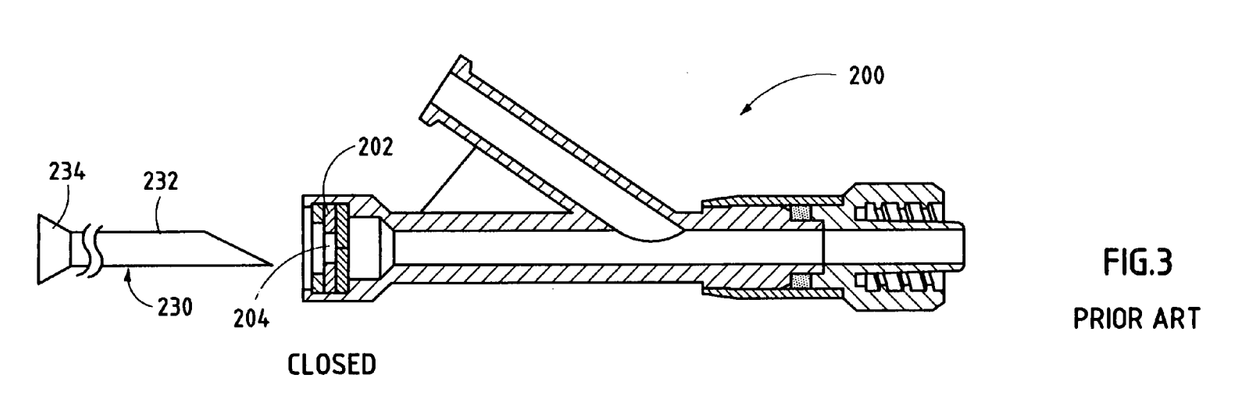
FIG. 3 shows a prior art valved connector of type 2 having a normally closed valve, with the valve shown in the closed rest position.
Figure 4:
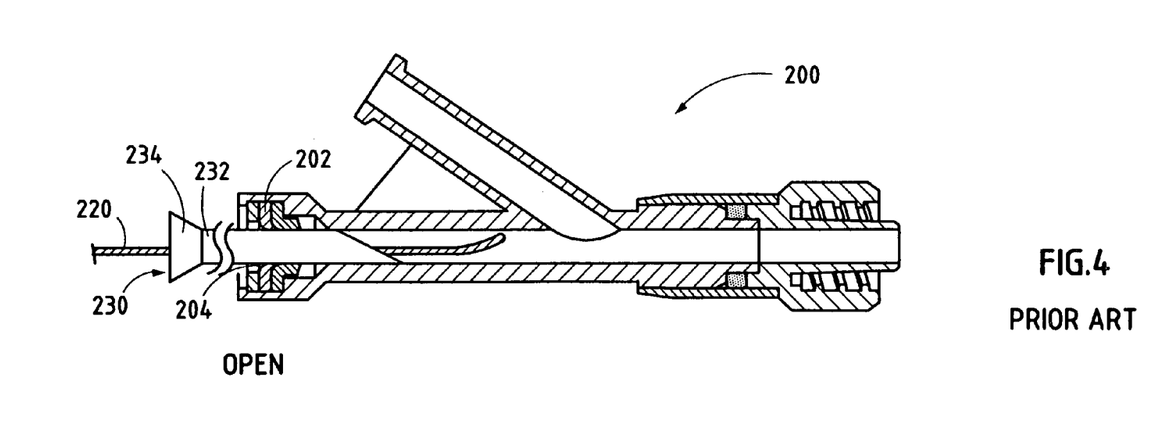
FIG. 4 shows the type 2 prior art valved connector of FIG. 3, shown with a separate tubular introducer inserted through the valve to open the valve for introduction of a secondary device.

The other type, referred to herein as type 2, includes a normally closed, passive or hemostatic valve which due to its elasticity and its cut or molded configuration, permits the passage of catheters while maintaining a seal without the necessity of manual adjustments, as shown in FIGS. 3 and 4. In this case, sealing is passive and continuous, and movement of catheter is possible due to the flexibility and the low friction of the valve. Nonetheless, the major problem of the type 2 system imposes itself during the introduction of fine and fragile instruments such as micro-guidewires and micro-catheters or assemblies mounted and maintained by friction or crimping, like for example a stent mounted on a balloon of a dilatation catheter. One must, in this case, utilize a small rigid introduction tube that is pushed across the valve and which permits introduction of fragile instruments through the valve. This tube is then removed and the valve seals around the proximal body of the instrument. The introduction tube remains, of course, in a coaxial position on the proximal body of the catheter introduced and can then cause difficulties for the operator. One foreseeable solution to avoid this problem is using a split introduction tube. However, such a split introduction tube is more fragile and less effective at crossing the valve and protecting the inserted instrument.

Another solution to this problem is to integrate the introduction tube into the connector device. This solution is illustrated in the following patent: U.S. Pat. No. 5,195,980. In this patent, a fitting with a tubular extension is slidably mounted on the proximal end of the valved connector. Sliding the fitting distally with respect to the valved connector causes the tubular extension to penetrate the valve and open it for passage of fluids or instruments. This solution, however, poses two other problems. First, the additional fitting and the tubular extension elongate the valved connector unnecessarily, requiring all of the inserted catheters and instruments to be that much longer, as well. Second, the configuration of these connectors creates internal steps or cavities within the connector that may impede, divert or damage a catheter or instrument during insertion and that may also create a nidus for stagnation and clotting of blood.

SUMMARY OF THE INVENTION

Therefore, it is a principal object of the present invention to resolve the technical problems in the prior art by providing a valved connector that provides the passive sealing advantages of the type 2, normally closed, hemostasis valve, together with the advantages of the type 1 valve in providing an open passage for safe introduction of extremely flexible or fragile catheters and instruments.

In addition, it is an object of the present invention to resolve another technical problem in the prior art by providing a valved connector with an integral closure system for opening and closing the hemostasis valve with a simple motion by the operator, in particular without employing a separate tool or external piece.

The present invention permits simultaneous resolution of these technical problems in a manner that is simple and low cost, and is usable in both an industrial and a medical setting.

In accordance with these objects, the present invention takes the form of a valved connector comprising:

a connector body having a tubular portion extending therefrom; and a valve body including a valve element with a passage therethrough, said valve body being axially movably with respect to said connector body;

wherein said valve body is movable from a closed position in which said tubular portion of said connector body is exterior to said passage of said valve element to an open position in which said tubular portion of said connector body is applied against said valve element to open at least partially said valve element.

Preferably, the connector has a normally closed, passive hemostasis valve with an integral closure system for opening and closing the hemostasis valve with a simple axial sliding motion. Preferably, the body of the valved connector apparatus is in a Y-shaped configuration with a main channel and a lateral channel branching off of the main channel. The hemostasis valve is housed in a valve body that is slidably connected to the proximal end of the main channel. The hemostasis valve is opened by sliding the valve body distally with respect to the Y-shaped connector body so that a cylindrical extension extending from the proximal end of the main channel of the connector body penetrates a central opening in the hemostasis valve, creating an open passage for insertion of guidewires, catheters or other instruments.

The configuration of the valved connector eliminates all internal steps and cavities within the connector that might impede, divert or damage a catheter or instrument during insertion or that would create a nidus for stagnation and clotting of blood. In addition, the configuration of the closure system does not require any additional length to be added to the connector body.

Other objects, characteristics and advantages of the invention will appear clearly in light of the description which follows made in reference to the drawings.

DETAILED DESCRIPTION OF THE INVENTION

FIG. 1 shows a known prior art valved connector 100, which is designated herein as type 1. The type 1 valved connector is commonly known as a compression fitting, and sometimes also as a Touhy-Borst fitting. The valve element of the connector 100 is a cylindrical or toroidal elastomeric seal 102 with an open passage 104 through the center of the seal 102. The valve element 102 is normally open in its rest position as shown in FIG. 1, which allows introduction of a secondary device 120 through the open passage 104 in the center of the seal 102. The open passage 104 facilitates the introduction of fragile devices, such as micro-guidewires and micro-catheters, however it allows back bleeding through the valved connector 100 when in the open position. In addition, many of the commercially available type 1 valved connectors include internal steps or blind spots in the body 106 of the connector 100 that may make it difficult to insert the secondary device 120 all the way through the valved connector 100, particularly if the distal end of the secondary device 120 has a preshaped curve. Furthermore, if the secondary device 120 has a tertiary device, such as a vascular stent, frictionally mounted on its exterior, the tertiary device may be moved or dislodged by contact with any internal steps or edges within the body 106 of the connector 100.

FIG. 2 shows the type 1 prior art valved connector 100 of FIG. 1, with the valve element 102 shown in the closed position to seal around a secondary device 120 introduced through the valved connector 100. The valved connector 100 includes a threaded cap 108 with an open passage 110 through the center of the cap 108. The threaded cap 108 screws into the body 106 of the connector 100 to axially compress the elastomeric seal 102, which closes the passage 104 through the center of the seal 102. The threaded cap 108 can be tightened to close the elastomeric seal 102 around a catheter, guidewire or other instrument or it may be tightened to completely close the valve element 102 when there is no secondary device inserted. The threaded cap 108 must be adjusted carefully to create an effective seal without crushing the secondary device 120, particularly if the secondary device 120 is a fragile micro-catheter. Typically, the threaded cap 108 must be loosened to allow axial movement of the secondary device 120 within the valve 102, which encourages the possibility of back bleeding. Movement of the secondary device 120 without loosening the threaded cap 108 can easily damage the secondary device 120, particularly if it is a fragile or highly flexible catheter or instrument.

The type 1 valved connector 100 has the additional disadvantage that the active sealing mechanism of the valve element 102 requires a complex turning motion of the threaded cap 108 to open or close the elastomeric seal 102. Turning the threaded cap 108 is further complicated when a fragile secondary device 120 is inserted through the threaded cap 108 and when the area is inevitably obscured with blood.

FIG. 3 shows another known prior art valved connector 200, which is designated herein as type 2. The type 2 valved connector is commonly known as a passive valve or hemostatic valve. The valve element of the connector 200 is an elastomeric seal 202 with a central passage 204 for introduction of a secondary device. In known type 2 valved connectors 200, the elastomeric seal 202 typically includes one, two or three stacked elastomeric seal elements that are each perforated or slit in a selected pattern to create a self-sealing central passage 204. The valve element 202 is normally closed when in its rest position, as shown in FIG.

3, so that it will passively seal to stop bleeding when the central passage 204 is empty and when a secondary device is inserted through the central passage 204. Because the valve element 202 is normally closed, it can be very difficult to introduce fragile or highly flexible secondary devices through the central passage 204 without damaging them. This difficulty is further exacerbated if the distal end of the secondary device has a preshaped curve or if there is a tertiary device, such as a vascular stent, frictionally mounted on the exterior of the secondary device.

To overcome this difficulty, a separate tubular introducer 230 may be used to introduce a secondary device 220 through the valved connector 200. FIG. 4 shows the type 2 prior art valved connector 200 of FIG. 3 with the separate tubular introducer 230 inserted through the valve element 202 to open the central passage 204 for introduction of the secondary device 220. The tubular introducer 230 has a central lumen 232 and may optionally have a funnel-shaped proximal end 234. The secondary device 220 is inserted through the central lumen 232 of the tubular introducer 230, then the tubular introducer 230 is withdrawn from the valved connector 200. While this facilitates the introduction of fragile or highly flexible secondary devices, it has the inconvenience that the tubular introducer 230 remains in place on the proximal part of the secondary device 220 where it may interfere with manipulations of the device 220 and where it reduces the effective usable length of the device 220. To overcome this problem, a slitted tubular introducer may be used so that it can be removed from the secondary device 220 after its introduction through the valved connector 200. However, such a slitted tubular introducer is itself somewhat fragile and may have difficulty crossing the elastomeric seal 202 and may not afford sufficient protection to the secondary device 220 as it is introduced through the central passage 204 of the seal 202.

Figure 5:
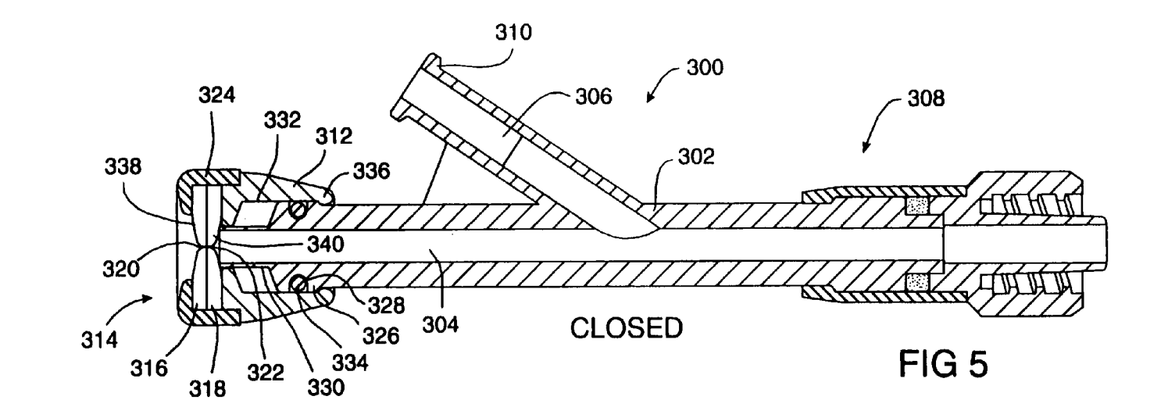
FIG. 5 shows a first embodiment of a valved connector apparatus constructed according to the present invention, with the valve shown in the normally closed position.

FIG. 5 shows a first embodiment of a valved connector apparatus 300 constructed according to the present invention. The valved connector apparatus 300 may take any one of many possible physical configurations. For example, the valved connector apparatus 300 may be integrated into the proximal end of another device, such as a catheter, a guiding catheter, an introducer sheath or a surgical access cannula. Alternatively, the valved connector apparatus 300 may be configured as a separate component that is adapted for attachment to another device, such as a catheter, a guiding catheter, an introducer sheath or a surgical access cannula. In one particularly preferred embodiment of the invention, illustrated in FIG. 5, the valved connector apparatus 300 is configured with a Y-shaped connector body 302 having a main channel 304 and a lateral channel 306 branching off of the main channel 304. Preferably, the inner diameter of the main channel 304 is smooth and continuous all the way through the Y-shaped connector body 302 without abrupt steps, exposed edges or severe tapers. Preferably, the Y-shaped connector body 302 has, on its distal end, an attachment mechanism 308, such as a rotatable male luer lock fitting or the like, connected to the main channel 304 for attaching the valved connector apparatus 300 to another device, such as a catheter, a guiding catheter, an introducer sheath or a surgical access cannula. The proximal end of the main channel 304 has a cylindrical ridge or boss 326 having an annular groove 328 in which a toroidal O-ring 334 or other sliding seal resides. A tubular thin-walled cylindrical extension 330 extends proximally of the cylindrical boss 326. The proximal end of the lateral channel 306 preferably has a second attachment mechanism 310, such as a female luer lock fitting or the like, for attaching to another device, such as a syringe or a connector tube. Preferably, the Y-shaped connector body 302 is injection molded of a rigid, transparent medical grade plastic, such as polycarbonate, polymethyl methacrylate, polystyrene or the like.

A valve body 312 is mounted on the proximal end of the main channel 304 of the Y-shaped connector body 302. The valve body 312 has an internal bore 332 that has a sliding fit with the cylindrical boss 326 on the proximal end of the main channel 304, and the valve body 312 is axially movable with respect to the Y-shaped connector body 302. The toroidal O-ring 334 creates a sliding seal between the valve body 312 and cylindrical boss 326. An internal ridge 336 on the distal edge of the internal bore 332 of the valve body 312 snaps over the cylindrical boss 326 and serves as a detent to limit the axial motion of the valve body 312 in the proximal direction. A hemostatic valve 314 with a central passage 320, 322 therethrough is mounted within the valve body 312. An annular valve cap 324 holds the hemostatic valve 314 in place within the valve body 312. The valve cap 324 may be attached to the valve body 312 with a friction fit, a snap fit, screw threads, an adhesive or it may be welded in place, for example by ultrasonic welding.

Any known passive hemostatic valve construction may be used for the hemostatic valve 314 of the valved connector apparatus 300. By way of example, FIG. 5 illustrates a hemostatic valve 314 that includes a first disk-shaped valve element 316 with a proximal portion of the central passage 320 extending therethrough and a second disk-shaped valve element 318 with a distal portion of the central passage 322 extending therethrough. In one exemplary embodiment, the proximal portion of the central passage 320 is defined by a circular perforation through the first valve element 316, and the distal portion of the central passage 322 is defined by a Y-shaped slit through the second valve element 318 and aligned with the circular perforation. In another exemplary embodiment, the proximal portion of the central passage 320 is defined by a first linear slit through the first valve element 316, and the distal portion of the central passage 322 is defined by a second linear slit through the second valve element 318 and aligned at a right angle to the first linear slit. Whatever the configuration of the slits or perforations, the first valve element 316 and the second valve element 318 are preferably made of an elastomeric material, such as silicone, latex, polyurethane or an injection moldable thermoplastic elastomer. Optionally, a small amount of biocompatible lubricant, such as silicone oil, may be placed on the valve elements 316, 318 to reduce the friction through the central passage 320, 322 of the hemostatic valve 314. Alternatively, a low friction coating or a self-lubricating material may be used for the valve elements 316, 318. Additionally, a shallow conical indentation 338, 340 may be formed on the proximal side of the first valve element 316 and/or the distal side of the second valve element 318, to lower the threshold force required to open the central passage 320, 322 of the hemostatic valve 314.

Figure 6:
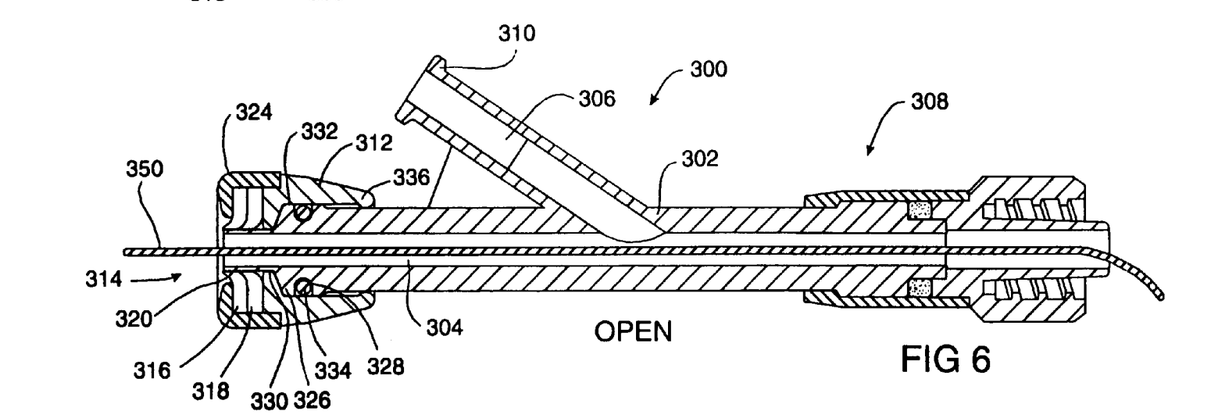
FIG. 6 shows the valved connector apparatus of FIG. 5, shown with the device actuated to open the valve for introduction of a secondary device.

When the valved connector apparatus 300 is in its normally closed resting position, as illustrated in FIG. 5, the valve body 312 is in its most proximal position with respect to the Y-shaped connector body 302. The proximal edge of the thin-walled cylindrical extension 330 presses against the distal side of the second valve element 318 with a small amount of compression force to form a seal where they contact one another. To open the central passage 320, 322 of the hemostatic valve 314, the valve body 312 is moved distally with respect to the Y-shaped connector body 302, as shown in FIG. 6. Preferably, the movement of the valve body 312 over the cylindrical boss 326 of the Y-shaped connector body 302 is accomplished with a simple axial sliding motion. Alternatively, the valve body 312 may be threaded to the cylindrical boss 326, preferably with a coarse pitch thread, so that rotating the valve body 312 will move it axially with respect to the Y-shaped connector body 302. When the valve body 312 is moved distally, the thin-walled cylindrical extension 330 penetrates the central passage 322, 320 from the distal to the proximal side of the hemostatic valve 314. With the central passage 320, 322 of the hemostatic valve 314 thus opened, a secondary device 350 may be easily introduced through the valved connector apparatus 300. Once the secondary device 350 is through the valved connector apparatus 300, the valve body 312 is moved proximally with respect to the Y-shaped connector body 302 to close the hemostatic valve 314, which seals around the proximal portion of the secondary device 350.

When the secondary device to be introduced is of a reduced size, it is possible to move the valve body of a length less than the displacement corresponding to the full opening of the valve element. In this case, the end of the tubular portion is applied against the valve element to produce a partial opening of the valve element.

Because the motion to open and close the hemostatic valve 314 is so quick and simple, there will be very little back bleeding through the hemostatic valve 314 in the short time that the central passage 320, 322 is open. Also, because the hemostatic valve 314 seals passively, it does not have to be reopened or loosened for maneuvering of the secondary device 350, which further reduces the chances of back bleeding. Another advantage of the passive sealing of the hemostatic valve 314 is that the valved connector apparatus 300 can be operated as a standard passive sealing hemostatic valve when inserting more robust instruments and catheters and while removing instruments and catheters, even, in some cases, more fragile instruments and catheters. When removing a fragile instrument or catheter that cannot tolerate being withdrawn through the closed hemostatic valve 314, for example a stent delivery catheter that still has a stent mounted on its exterior, the central passage 320, 322 may be reopened by simple pushing the valve body 312 distally with respect to the Y-shaped connector body 302.

Figure 7:
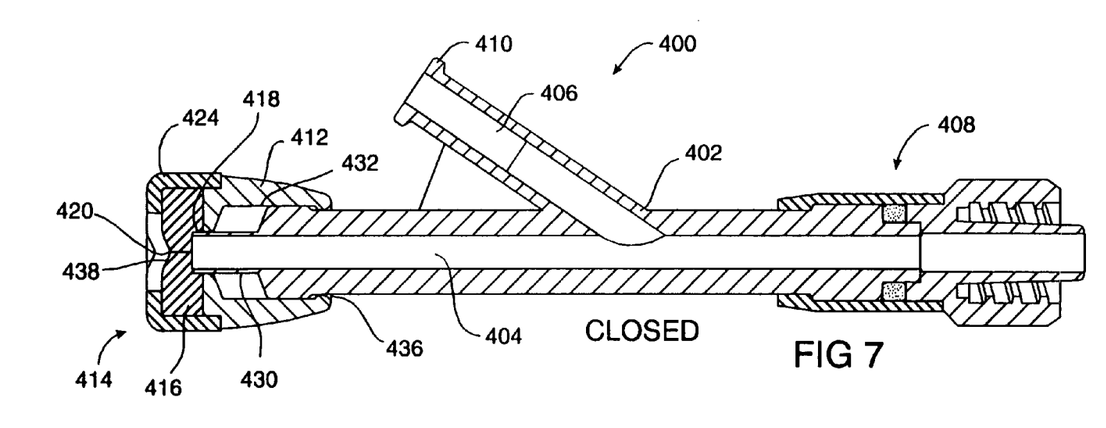
FIG. 7 shows a second embodiment of a valved connector apparatus constructed according to the present invention, with the valve shown in the normally closed position.

FIG. 7 shows a second embodiment of a valved connector apparatus 400 constructed according to the present invention. As with the previously described embodiment, the valved connector apparatus 400 may take any one of many possible physical configurations, including as a separate or integral component for use with a catheter, a guiding catheter, an introducer sheath or a surgical access cannula. A particularly preferred embodiment of the invention is illustrated in FIG. 7 having a Y-shaped connector body 402 with a main channel 404 and a lateral channel 406 branching off of the main channel 404. The inner diameter of the main channel 404 is preferably smooth and continuous all the way through the Y-shaped connector body 402 without abrupt steps, exposed edges or severe tapers. The Y-shaped connector body 402 has a first attachment mechanism 408, such as a rotatable male luer lock fitting or the like, connected to the distal end of the main channel 404, and a second attachment mechanism 410, such as a female luer lock fitting or the like, connected to the proximal end of the lateral channel 406, for attachment to another device, such as a catheter, a guiding catheter, an introducer sheath, a surgical access cannula, a syringe or a connector tube. The proximal end of the main channel 404 has a cylindrical ridge or boss 426 and a tubular thin-walled cylindrical extension 430 extending proximally of the cylindrical boss 426. The Y-shaped connector body 402 is preferably injection molded of a rigid, transparent medical grade plastic, such as polycarbonate, polymethyl methacrylate, polystyrene or the like.

A valve body 412 is mounted on the proximal end of the main channel 404 of the Y-shaped connector body 402. The valve body 412 has an internal bore 432 that has a sliding fit with the cylindrical boss 426 on the proximal end of the main channel 404, and the valve body 412 is axially movable with respect to the Y-shaped connector body 402. An internal ridge 436 on the distal edge of the internal bore 432 of the valve body 412 snaps over the cylindrical boss 426 and serves as a detent to limit the axial motion of the valve body 412 in the proximal direction. A hemostatic valve 414 with a central passage 420 therethrough is mounted within the valve body 412. An annular valve cap 424 holds the hemostatic valve 414 in place within the valve body 412. The valve cap 424 may be attached to the valve body 412 with a friction fit, a snap fit, screw threads, an adhesive or it may be welded in place, for example by ultrasonic welding.

The hemostatic valve 414 in this embodiment of the valved connector apparatus 400 has a single-piece valve element 416 injection molded of an elastomeric material, such as silicone, latex, polyurethane or an injection moldable thermoplastic elastomer. The single-piece valve element 416 has a generally cylindrical external shape with a central bore 418 that is axially aligned with the central passage 420. The central bore 418 has a sliding interference fit with the thin-walled cylindrical extension 430 of the Y-shaped connector body 402 so that a sliding fluid tight seal is created where they contact one another. Similar to the previously described embodiment, the central passage 420 of the valve element 416 may be defined by a circular perforation on the proximal side in alignment with a Y-shaped slit on the distal side, or by a first linear slit on the proximal side aligned at a right angle to a second linear slit on the distal side, or other known hemostasis valve structure. The slits or perforations may be molded into the valve element 416 or they may be cut into the valve element 416 after it is injection molded. Optionally, a small amount of biocompatible lubricant, such as silicone oil, may be placed on the valve element 416 to reduce the friction through the central passage 420 of the hemostatic valve 414. Alternatively, a low friction coating or a self-lubricating material may be used for the valve element 416. Additionally, a shallow conical indentation 438 may be formed on the proximal and/or distal surface of the valve element 416, to lower the threshold force required to open the central passage 420 of the hemostatic valve 414.

Figure 8:
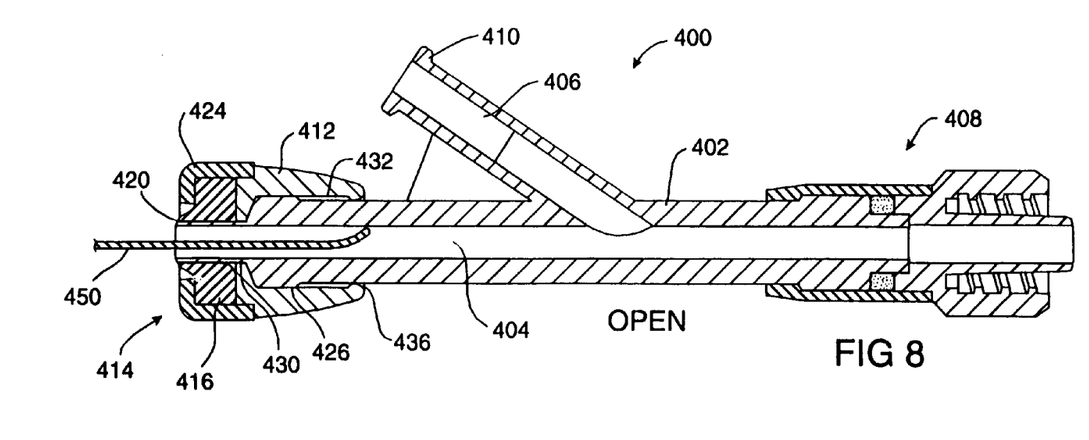
FIG. 8 shows the valved connector apparatus of FIG. 7, shown with the device actuated to open the valve for introduction of a secondary device.

When the valved connector apparatus 400 is in its normally closed resting position, as illustrated in FIG. 7, the valve body 412 is in its most proximal position with respect to the Y-shaped connector body 402. The proximal end of the thin-walled cylindrical extension 430 forms a sliding fluid tight seal within the central bore 418 of the valve element 416. To open the central passage 420 of the hemostatic valve 414, the valve body 412 is moved distally with respect to the Y-shaped connector body 402, as shown in FIG. 8, preferably using a simple axial sliding motion. When the valve body 412 is moved distally, the thin-walled cylindrical extension 430 penetrates the central passage 420 from the distal to the proximal side of the hemostatic valve 414. With the central passage 420 of the hemostatic valve 414 thus opened, a secondary device 450 may be easily introduced through the valved connector apparatus 400. Once the secondary device 450 is through the valved connector apparatus 400, the valve body 412 is moved proximally with respect to the Y-shaped connector body 402 to close the hemostatic valve 414, which seals around the proximal portion of the secondary device 450. The hemostatic valve 414 can be easily reopened by pushing the valve body 412 distally with respect to the Y-shaped connector body 402 for withdrawing the secondary device 450.

As with the previously described embodiment, the simple motion to open and close the hemostatic valve 414 allows it to be opened and closed very quickly so that there will be very little back bleeding through the hemostatic valve 414 in the short time that the central passage 420 is open. The passive sealing of the valved connector apparatus 400 allows maneuvering of the secondary device 450 without reopening or loosening the hemostatic valve 414. Also, the hemostatic valve 414 can be operated as a standard passive sealing hemostatic valve when inserting or removing more robust instruments and catheters.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A valved connector, comprising:
    a connector body having a tubular portion extending proximally therefrom, said tubular portion having a proximal end and a distal end; and
    a valve body including a valve element with a passage therethrough, said valve body being axially movable with respect to said connector body,
    wherein said valve body is movable from a closed position in which said tubular portion of said connector body is external to said passage of said valve element to an open position in which said tubular portion of said connector body extends through said valve element from a distal side to a proximal side to open said valve element and wherein said proximal end of said tubular portion is exposed on the exterior of said valved connector thereby providing an open channel for introducing a secondary device to be inserted through said connector body.

2. The valved connector of claim 1, wherein said connector body is configured in a Y-shape with a main channel and a lateral channel branching therefrom, said valve body being positioned at a proximal end of said main channel, said connector body having a first attachment means at a distal end of said main channel and a second attachment means at a proximal end of said lateral channel.

3. The valved connector of claim 2, wherein said first attachment means comprises a male luer lock connector and said second attachment means comprises a female luer lock connector.

4. The valved connector of claim 1, wherein when said valve body is in said closed position said passage of said valve element closes to form a fluid tight seal.

5. The valved connector of claim 1, wherein when said valve body is in said open position said connector body presents an uninterrupted channel without obstacles for introducing a secondary device inserted through said connector body.

6. The valved connector of claim 1, wherein when said valve body is in said closed position said passage of said valve element closes to form a fluid tight seal around a secondary device inserted through said passage.

7. The valved connector of claim 1, further comprising a sliding seal between said valve body and said connector body.

8. The valved connector of claim 1, further comprising a sliding seal between said valve element and said tubular portion extending from said connector body.

9. The valved connector of claim 1, wherein said valve element is made of an elastomeric material.

10. The valved connector of claim 1, wherein the connector body has a proximal end with a cylindrical boss having an annular groove therein, the tubular portion extending proximally from the cylindrical boss, the valve body having an internal bore having a sliding fit with the cylindrical boss on the proximal end of the connector body, a toroidal O-ring within the annular groove forming a fluidtight sliding seal between the valve body and cylindrical boss, a detent on a distal end of the internal bore of the valve body to limit the axial motion of the valve body in the proximal direction with respect to the cylindrical boss.

11. The valved connector of claim 1, wherein the connector body has a proximal end with a cylindrical boss, the tubular portion extending proximally from the cylindrical boss, the valve body having an internal bore having a sliding fit with the cylindrical boss on the proximal end of the connector body, a detent on a distal end of the internal bore of the valve body to limit the axial motion of the valve body in the proximal direction with respect to the cylindrical boss, the valve element configured with a central bore that is axially aligned with the passage therethrough, the central bore having a sliding fit with the tubular portion of the connector body forming a fluidtight sliding seal between the tubular portion and the valve element.

12. A valved connector, comprising:
    a connector body having a tubular portion extending proximally therefrom, said tubular portion having a proximal end and a distal end, and
    a valve body including a valve element with a passage therethrough, said valve body being positioned at a proximal end of said connector body and axially movable with respect to said connector body,
    wherein said valve body is movable from a closed position in which said tubular portion of said connector body is external to said passage of said valve element to an open position in which said tubular portion of said connector body extends through said passage of said valve element from a distal side to a proximal side of said valve element, wherein when said valve body is in said closed position said passage of said valve element closes to form a fluid tight seal, wherein when said valve body is in said open position said proximal end of said tubular portion is exposed on the exterior of said valved connector thereby providing an open channel for introducing a secondary device to be inserted through said connector body, and wherein when said valve body is in said closed position with the secondary device inserted therethrough, said passage of said valve element closes to form a fluid tight seal around the secondary device.

13. The valved connector of claim 12, further comprising a sliding seal between said valve body and said connector body.

14. The valved connector of claim 12, further comprising a sliding seal between said valve element and said tubular portion extending from said connector body.

15. The valved connector of claim 12, wherein said valve element is made of an elastomeric material.

16. The valved connector of claim 12, wherein said connector body is configured in a Y-shape with a main channel and a lateral channel branching therefrom, said valve body being positioned at a proximal end of said main channel, said connector body having a first attachment means at a distal end of said main channel and a second attachment means at a proximal end of said lateral channel.

17. The valved connector of claim 16, wherein said first attachment means comprises a male luer lock connector and said second attachment means comprises a female luer lock connector.

18. The valved connector of claim 16, wherein said first attachment means comprises a rotating male luer lock connector and said second attachment means comprises a female luer lock connector.

19. The valved connector of claim 16, wherein the connector body is configured with a cylindrical boss on the proximal end of the main channel, the tubular portion extending proximally from the cylindrical boss, the valve body having an internal bore having a sliding fit with the cylindrical boss, the cylindrical boss having an annular groove with a toroidal O-ring within the annular groove forming a fluidtight sliding seal between the valve body and the cylindrical boss, a detent on a distal end of the internal bore of the valve body to limit the axial motion of the valve body in the proximal direction with respect to the cylindrical boss.

20. The valved connector of claim 16, wherein the connector body is configured with a cylindrical boss on the proximal end of the main channel, the tubular portion extending proximally from the cylindrical boss, the valve body having an internal bore having a sliding fit with the cylindrical boss, a detent on a distal end of the internal bore of the valve body to limit the axial motion of the valve body in the proximal direction with respect to the cylindrical boss, the valve element configured with a central bore that is axially aligned with the passage therethrough, the central bore having a sliding fit with the tubular portion of the connector body forming a fluidtight sliding seal between the tubular portion and the valve element.

21. The valved connector of claim 1, wherein the valve body is threaded to the connector body, such that rotating the valve body moves the valve body axially with respect to the connector body.

* * * * *